US006805862B1

(12) United States Patent
Chapman et al.

(10) Patent No.: US 6,805,862 B1
(45) Date of Patent: Oct. 19, 2004

(54) ANTI-IDIOTYPIC ANTIBODY WHICH INDUCES AN IMMUNE RESPONSE AGAINST A GLYCOSPHINGOLIPID AND USE THEREOF

(75) Inventors: Paul B. Chapman, New York, NY (US); Alan N. Houghton, New York, NY (US)

(73) Assignee: Sloan-Kattering Institute For Cancer Research, New York, NY (US)

( * ) Notice: Subject to any disclaimer, the term of this patent is extended or adjusted under 35 U.S.C. 154(b) by 0 days.

(21) Appl. No.: 08/488,549

(22) Filed: Jun. 7, 1995

Related U.S. Application Data

(60) Division of application No. 08/447,412, filed on May 23, 1995, now Pat. No. 6,432,402, which is a continuation of application No. 08/218,316, filed on Mar. 25, 1994, now abandoned, which is a continuation of application No. 07/776,266, filed on Jan. 27, 1992, now abandoned, which is a continuation of application No. PCT/US90/03061, filed on May 25, 1990, which is a continuation-in-part of application No. 07/357,037, filed on May 25, 1989, now abandoned.

(51) Int. Cl.$^7$ ...................... A61K 39/395; A61K 39/00; C07K 16/00; C07K 16/28; C07K 21/08

(52) U.S. Cl. ................. 424/131.1; 424/137.1; 424/184.1; 424/143.1; 424/155.1; 530/387.2; 530/387.7; 530/388.8; 530/388.85; 514/885

(58) Field of Search .................... 424/131.1, 137.1, 424/182.1, 184.1, 143.1, 155.1; 530/387.2, 388.8, 388.85; 514/885

(56) References Cited

U.S. PATENT DOCUMENTS

| | | | |
|---|---|---|---|
| RE32,833 E | 1/1989 | Green et al. | |
| 4,849,509 A | 7/1989 | Thurin et al. | |
| 4,900,547 A | 2/1990 | Levy et al. | |
| 4,918,164 A | 4/1990 | Hellstrom et al. | |
| 5,126,262 A | 6/1992 | Matsui et al. | |
| 5,270,202 A | 12/1993 | Raychaudhuri | |
| 5,493,009 A | 2/1996 | Ferrone | |
| 5,529,922 A | 6/1996 | Chapman et al. | |
| 5,792,455 A | 8/1998 | Chapman et al. | |

FOREIGN PATENT DOCUMENTS

| | | |
|---|---|---|
| EP | 0134868 | 3/1985 |
| EP | 0306995 | 3/1989 |
| EP | 0473721 | 12/1998 |
| WO | WO A 8706840 | 11/1987 |
| WO | WO A 8808429 | 11/1988 |
| WO | WO14104 | 11/1990 |

OTHER PUBLICATIONS

Miller, Proc. 11$^{th}$ Annual Cancer Symposium. Scripps Memorial Hospitals Cancer Center p. 3–5, 1987.*

Irie et al Advances in the Biology and Clinical Management of Melanoma 35$^{th}$ Annual Clinical Conference & Twenty-fourth Annual Special Pathology Program Nov. 20–23, 1991, pp. 46–47, 1991.*

Houghton et al PNAS vol. 82, pp. 1242–1246, Feb. (1985).*

Tsuchida et al, J. Natl Cancer Inst. Jan. (1987) vol. 78, p. 45–54.*

Vitetta et al. Science vol. 238, pp. 1098–1104, Nov. 20, 1987.*

Bucholtz Seminars in Oncol. SVurs. vol. 3, No. 1 pp. 67–73 (1989).*

Chapman, P.B., et al. (1993) "Use of BEC2 anti–idiotypic monoclonal antibody (MAb) to induce antibodies against GD3 ganglioside in melanoma patients", Proc. Annu. Meet. Am. Soc. Clin. Oncol., 12:A1323 (Exhibit 3).

Chapman, P.B., et al., (1994) "Immunization of Melanoma Patients Against G–D3 Ganglioside With BEC2, an Anti–Idiotypic Monoclonal Antibody", *Cancer Biotherapy*, 9(1):95–96, Abstract. (Exhibit 4).

Grant, S.C., et al., (1996) "Long Survival following Immunization with BEC2 plus BCG after Initial Therapy for Small Cell Lung Cancer (SCLC)", Proc. Annu. Meet. Am. Soc. Clin. Oncol., 15:A1806. (Exhibit 5).

Mittleman, A., et al., (1992) "Human High Molecular Weight Melanoma–Associated Antigen (HMW–MAA) Mimicry by Mouse Anti–Idiotypic Monoclonal Antibody MK2–23: Induction of Humoral Anti–HMW–MAA Immunity and Prolongation of Survival in Patients with Stage IV Melanoma", *Proceedings of the National Academy of Sciences of the United States of America*, 89(2):466–470. (Exhibit 6).

Mittleman, A., et al., (1990) "Anti–Idiotypic Monoclonal Antibodies in Patients with Malignant Melanoma Enhancement of Their Immunogenicity by Conjugates to KLH and BCG", *Clinical Research*, 38(2), 549A, Abstract. (Exhibit 7).

Morrision et al., "Genetically Engineered Antibody Molecules and Their Application," *Annals of the New York Academy of Sciences*, 507:187–198 (1987).

(List continued on next page.)

*Primary Examiner*—Geetha P. Bansal
(74) *Attorney, Agent, or Firm*—John P. White; Cooper & Dunham LLP

(57) ABSTRACT

The present invention provides an anti-idiotypic monoclonal antibody which specifically induces an immune response against a glycosphingolipid. Additionally, this invention provides a method of producing the anti-idiotypic monoclonal antibody. Finally, this invention provides a composition of matter comprising an effective amount of a cytokine and a melanoma ganglio-side-specific antibody attached to a carrier.

1 Claim, 11 Drawing Sheets

OTHER PUBLICATIONS

Real et al., "Surface Antigens of Melanomas and Melanocyets Defined by Mouse Monoclonal Antibodies: Specificity Analysis and Comparison of Antigen Expression in Cultured Cells and Tissues," Cancer Research, 45: 4401–4411 (1985).

Tao et al., "Studies of Aglycosylated Chimeric Mouse–Human IgG: Role of Carbohydrate in the Structure and Effector Functions Mediated by the Human IgG Constant Region," The Journal of Immunology, 143:2595–2601 (1989).

Viale G., et al., "Anti–human Tumor Antibodies Induced In Mice And Rabbits By "Internal Image" Anti–idiotypic Monoclonal Immunoglobulins", J. Immunology, Dec. 15, 1987, vol. 139, pp. 4250–4255.

Wei, W–Z., et al., "Improved Anti–tumor Reactivity With Monoclonal Anti–idiotypic Antibody Conjugated To Syngeneic Mouse Red Blood Cells", J. Immunology Methods, 1989, vol. 122, pp. 227–234.

European Search Report, published Oct. 10, 1998 (Exhibit 1).

Chapman et al. "Pilot Trial of Anti–Idiotypic Monoclonal Antibody BEC2 in Patients with Metastatic Melanoma," Proceedings of the American Association for Cancer Research, vol. 33:208 (1992) (Exhibit 2).

Soderstrom, T. et al. "The Escherichia coli K1 Capsule Shares Antigenic Determinants with the Human Ganglioside GM3 and GD3" The New England Journal of Medicine, 310: 727–727 (1984) (Exhibit 3).

Burgess et al., "Possible Dissociation of the Heparin–binding and Mitogenic Activities of Heparin–binding (Acidic Fibroblast) Growth Factor–1 from Its Receptor–binding Activities by Site Directed Mutagenesis of a Single Lysine Residue" Journal of Cell Biology, 111:2129–2138 (1990).

Chapman et al., "Anti–idiotype vaccines", Biologic Therapy of Cancer Updates (1992) 2; 1–9 (review article).

Chapman, et al., (1993) "Use of BEC2 Anti–Idiotypic Monoclonal Antibody (Mab) To Induce Antibodies Against GD3 Ganglioside in Melanoma Patients," Proceedings of ASCO, vol. 12, 1323:388.

Forstrom J. W., et al., "Immunization To A Syngeneic Sarcoma By A Monoclonal Auto–anti–idiotypic Antibody", Nature, vol. 303, Jun. 16, 1983, pp. 627–629.

Gillies et al., "Antigen binding and biological activities of engineered mutant chimeric antibodies with human tumor specificities," Human Antibodies and Hybridomas 1:47–54 (1990).

Iwamori et al., "Comparative Study on Ganglioside Compositions of Various Rabbit Tissues Tissues Tissue–Specificity in Ganglioside Molecular Species of Rabbit Thymus," Biochimica et Biophysica Acta, 665:214–220 (1981).

Juy, D. and Chedid L. (1975) "Comparison between macrophage activation and enhancement of nonspecific resistance to tumors by mycobacterial immunoadjuvants" Immunology 72:4105–4109.

Koprowski H., et al., "Human Anti–idiotype Antibodies In Cancer Patients: Is The Modulation Of The Immune Response Beneficial For The Patient?", PNAS, Jan. 1984, vol. 81, pp. 216–219.

Kundu et al., "Preparation and Properties of Antibodies to GD3 and GM1 Gangliosides," Journal of Neurochemistry, 34(1): 184–188 (1980).

Lazar et al., "Transforming Growth Factor: Mutation of Aspartic Acid 47 and Leucine 48 Results in Different Biological Activities," Molecular and Cellular Biology, 8: 1247–1252 (1988).

Livingston, P.O. et al., (1987) "Vaccines containing purified GM2 ganglioside elicit GM2 antibodies in melanoma patients," Immunology 84: 2911–2915.

Anderson, et al., "Idiotype Network Responses to Murine Immunoglobulin G3 Anti–Carbohydrate Antibodies", Journal of Immunotherapy, 1992, vol. 11, pp. 267–273 (Exhibit 11).

Bentley, et al., "Three–dimensional Structure Of An Idiotope–anti–idiotope Complex", Nature 1990, vol. 348, pp. 254–257, (Exhibit 12).

Chapman, et al., "An Anti–idiotypic Monoclonal Antibody Carrying The Internal Image Of GD3 Ganglioside", Eightieth Annual Meeting Of The American Association For Cancer Research, Mar. 1989, vol. 30, p. 344 (Exhibit 13).

Cheresh, et al., "Disialoganglioside GD3 On Human Melenoma Serves As A Relevant Target Antigen For Monoclonal Antibody–mediated Tumor Cytolysis", PNAS 1985, vol. 82, pp. 5155–5159 (Exhibit 14).

Davis, et al., "Antibody and HIV–1 gp120 Recognition of CD4 Undermines The Concept of Mimicry Between Antibodies And Receptors", Nature 1992, vol. 358, pp. 76–79 (Exhibit 15).

Dippold, et al., "Cell Surface Antigens Of Human Malignant Melanoma: Definition of Six Antigenic Systems With Mouse Monoclonal Antibodies", PNAS, 1980, vol. 77:10, pp. 6114–6118.

Hastings, et al., "Production And Characterization Of A Murine/Human Chimeric Anti–idiotype Antibody That Mimics Ganglioside", Cancer Research, Apr. 1992, vol. 52, pp. 1681–1686 (Exhibit 16).

Hellstrom, "Strong Antitumor Activities Of IgG3 Antibodies To A Human Melanoma–associated Ganglioside", PNAS, Mar. 1985, vol. 82, pp. 1499–1502 (Exhibit 17).

Hird, et al., "Immunotherapy With Monoclonal Antibodies", Genes and Cancer, 1990, pp. 183–189 (Exhibit 18); Hodgson, "Making Monoclonals In Microbes", Biotechnology 1991, vol. 9, pp. 421–424 (Exhibit 19).

Houghton, et al., "Mouse Monoclonal IgG3 Antibody Detecting $G_{D3}$ Ganglioside: A Phase I Trial In Patients With Malignant Melanoma", PNAS 1985, vol. 82, pp. 1242–1246 (Exhibit 20).

Kerlin, et al., "Variations In Immunoglobulin Isotype Produced During The Antibody Response To Brucella Abortus and Staphylococcus Aureus Vaccines In Sheep", Research in Veterinary Science, 1986, vol. 41, p. 191 (Exhibit 21).

Livingston, et al., "Serological Response Of Melanoma Patients To Vaccines Prepared From VSV Lysates of Autologous and Allogenic Cultured Melanoma Cells", Cancer 1985, vol. 55, pp. 713–720.

Miller, et al., "Shared Idiotypes Expressed By Human B–Cell Lymphomas", New England Journal of Medicine, 1989, vol. 321, No. 13, p. 851–857 (Exhibit 22).

Morrison, et al., "Transfections Provide Novel Chimeric Antibodies", Science 1985, vol. 229, pp. 1202–1207.

Morrison, et al., "Production and Characterization of Genetically Engineered Antibody Molecules", Clinical Chemistry, 1988, vol. 34, pp. 1668–1675 (Exhibit 23).

Nepom, et al., "Anti–idiotypic Antibodies And The Induction Of Specific Tumor Immunity", Cancer and Metastasis Reviews, 1987, vol. 6, pp. 489–502.

Nepom, et al., "Induction Of Immunity To A Human Tumor Marker By In Vivo Administration Of Anti–idiotypic Antibodies In Mice", PNAS, vol. 81, May 1984, pp. 2864–2867 (Exhibit 24).

Oi, et al., "Chimeric Antibodies", Biotechniques 1986, vol. 4, pp. 214–221 (Exhibit 25).

Raychaudhuri, et al., "Generation And Characterization Of Internal Image Tumor Antigen", Journal Of Immunology 1986, vol. 137, No. 5, p. 1743 (Exhibit 26).

Saroj Vadhan–Raj, et al., "Phase I Trial Of A Mouse Monoclonal Antibody Against GD3 Ganglioside In Patients With Melanoma: Induction Of Inflammatory Response At Tumor Sites", Journal Of Clinical Oncology 1988, vol. 6, No. 10, pp. 1636–1648.

Schreiber, et al., "Anti–Idiotype Induced, LPS–Specific Antibody Response To Pseudomonas Aeruginosa", Clinical Research, 1988, vol. 36, No. 3.

Shin, "Production And Properties Of Chimeric Antibody Molecules", Methods in Enzymology, 1989, vol. 178, pp. 459–476 (Exhibit 27).

Soederstroem, et al., "The *Escherichia Coli* K1 Capsule Shares Antigenic Determinants With The Human Ganglioside GM3 and GD3", Chemical Abstracts, Jun. 1984, vol. 100, p. 425 (Exhibit 28).

Staruch, et al., "The Adjuvanticity Of Interleukin 1 In Vivo", Journal of Immunology 1983, vol. 130, pp. 2191 (Exhibit 29).

Stein, "Neonatal Administration Of Idiotype Or Antidiotype Primes For Protection Against *Escheria Coli* K13 Infection In Mice", Journal of Experimental Medicine 1984, vol. 160, pp. 1001–1011.

Tadashi, T., et al., "Immunogenicity Of Melanoma–associated Gangliosides In Cancer Patients", In. J. Cancer, 1985, vol. 35, pp. 607–612.

Viale, et al., "Idiotypic Replica Of An Anti–Human Tumor 15, Associated Antigen Monoclonal Antibody", J. Immunology, Dec. 1989, vol. 143, pp. 4338–4344.

Yeh, et al., "Mouse Monoclonal Anti–idiotypic Antibody To MG–21, A Mouse IgG3 Monoclonal Antibody To A Human Melanoma—Associated GD3 Ganglioside Antigen", Proceedings of AACR, Mar. 1987, vol. 28, p. 388, Abstract No. 1538 (Exhibit 30).

Young, et al., "Production Of Monoclonal Antibodies Specific For Two Distinct Steric Portions Of The Glycolipid Ganglio–*N*–Triosylceramide", Oct. 1979, Journal of Experimental Medicine, vol. 150, pp. 1008–1019 (Exhibit 31).

Waldmann, T., "Monoclonal Antibodies In Diagnosis And Therapy", Science, Jun. 1991, vol. 252, p. 1657–1662 (Exhibit 32).

* cited by examiner

FIGURE 2
Igm ANTI-GD$_3$ REACTIVITY
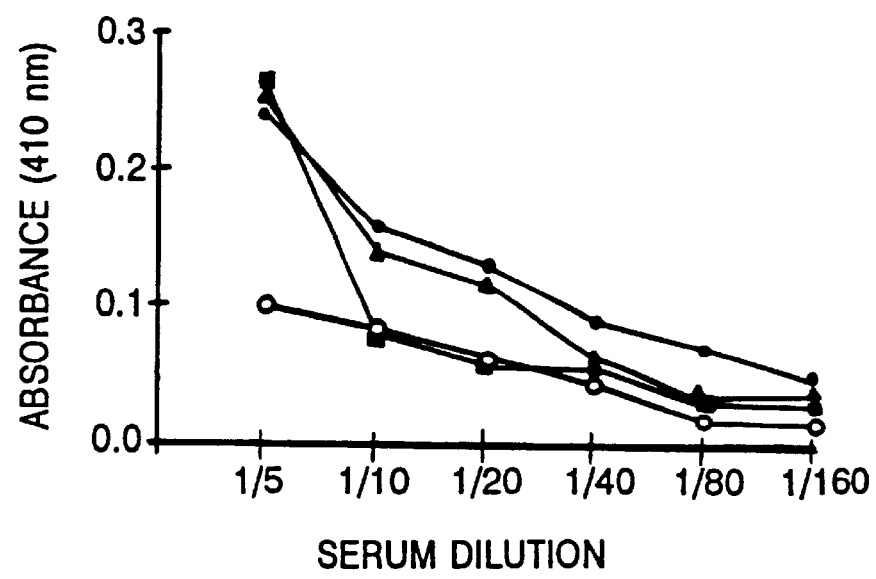
| | | No. of Booster Immunizations |
|---|---|---|
| ○—○ | Pre-Immune | 0 |
| ●—● | Day 31 | 1 |
| ▲—▲ | Day 43 | 2 |
| ■—■ | Day 67 | 3 |

*ANTI-GD₃ ANTIBODIES INDUCED BY BEC2 DO NOT CROSS-REACT WITH OTHER GANGLIOSIDES*

FIGURE 11
R24 VARIANTS
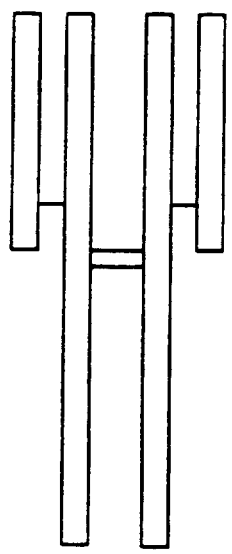 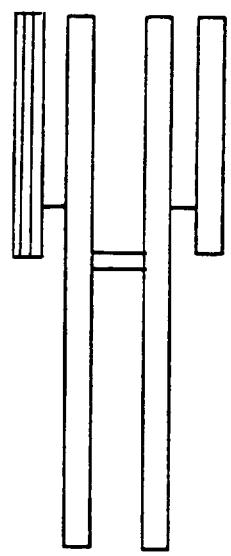 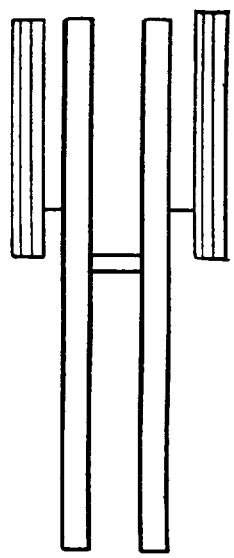
R24　　　　V2-R24　　　　V1-R24
Light Chain: R24
　　　　　　 NS-1

ANTI-IDIOTYPIC ANTIBODY WHICH INDUCES AN IMMUNE RESPONSE AGAINST A GLYCOSPHINGOLIPID AND USE THEREOF

This application is a divisional of U.S. Ser. No. 08/447,412, filed May 23, 1995 now, U.S. Pat. No. 6,432,402, which is a continuation of U.S. Ser. No. 08/218,316, filed Mar. 25, 1994 now abandoned; which is a continuation of U.S. Ser. No. 07/776,266 filed Jan. 27, 1992; now abandoned; which is a continuation Application of PCT International Application No. PCT/US90/03061, filed May 25, 1990, which is a continuation in part and claims priority of U.S. application Ser. No. 07/357,037, filed May 25, 1989, now abandoned.

BACKGROUND OF THE INVENTION

R24, an IgG3 mouse monoclonal antibody (mAb) raised against a human melanoma, recognizes the $GD_3$ ganglioside. The $GD_3$ ganglioside is abundantly expressed on most melanomas, however, expression of the $GD_3$ ganglioside on normal tissue is selective and occurs at low concentrations (1). Gangliosides are a subset of glycosphingolipids which in turn are a subset of glycolipids. Glycolipids, as their name implies, are sugar-containing lipids.

R24 comprises a known mixture of three variant antibody species (FIG. 11) designated V1-R24, V2-24, and R24. The V1-R24 and V2-R24 variants comprise one and two irrelevant antibody light chains, respectively; in contrast. R24 comprises relevant light chains. Generally, light and heavy antibody chains in combination effect specific antibody-antigen binding. However, antibodies comprising irrelevant antibody light chains, unlike antibodies comprising relevant antibody light chains, do not specifically bind an antigen.

In order to avoid confusion, the R24 variant from hereinafter will be referred to as "R24" and R24 comprising the three variant species will be referred to as the "R24 composition." Each variant exhibits differences which imply that the $GD_3$-binding region (also termed "paratope") of V1-R24, V2-R24, and R24 are altered.

Anti-idiotypic monoclonal antibodies which mimic and possess the internal image of a saccharidic epitope have been developed (2). The saccharidic epitope is a tumor associated globoside, i.e. a glycolipid. However, these anti-idiotypic (monoclonal antibodies do not specifically mimic a glycosphingolipid, a ganglioside, or more particularly the $GD_3$ ganglioside. Additionally, these anti-idiotypic monoclonal antibodies are not directed against R24 or any antibodies which specifically bind a glycosphingolipid or a ganglioside, let alone the $GD_3$ ganglioside.

Mice have been primed against capsular antigens of pathogenic bacteria by administration of monoclonal anti-idiotypic antibodies which mimic the polysaccharide capsule of E. coli (a gram negative bacteria) (3). It is generally known that lipopolysaccharides (LPS) is a major component of the outer membrane of gram negative bacteria and is released when bacteria are lysed. LPS consists of a heteropolysaccharide chain linked covalently to a glycolipid. It is important to point out that although these monoclonal anti-idiotypic antibodies were used as a means to prime a subject against a LPS, there is no suggestion of generating monoclonal anti-idiotypic antibodies against R24 or any antibodies which would specifically bind glycosphingolipids or gangliosides, in particular the $GD_3$ ganglioside.

The $GD_3$ ganglioside is poorly immunogenic (1). Accordingly, the $GD_3$ ganglioside is an appealing target for cancer immunotherapy because of the commercial utility of designing molecules which would structurally mimic $GD_3$ and possess dramatically significant immunogenic properties.

SUMMARY OF THE INVENTION

The present invention also provides an anti-idiotypic monoclonal antibody which specifically induces an immune response against a glycosphingolipid and more specifically against a ganglioside. Additionally, this invention provides a composition of matter comprising an effective amount of a cytokine and a melanoma ganglioside-specific antibody attached to a carrier. Finally, this invention provides a method of generating the previously-identified anti-idiotypic antibody which comprises: (a) preparing an antibody; (b) purifying the antibody; (c) attaching the antibody onto a carrier so as to produce an immunogen; (d) combining the immunogen with a cytokine so as to produce a novel immunogen-cytokine combination; and (e) injecting the novel immunogen-cytokine combination into a mammal thereby producing the anti-idiotypic antibody.

BRIEF DESCRIPTION OF THE FIGURES

FIG. 2: Anti-$GD_3$ reactivity induced in rabbits by immunization with BEC2. Rabbits were inoculated subcutaneously with 100 µl of BEC2 in complete Freund's adjuvant. Subsequent booster immunizations were administered either subcutaneously in incomplete Freund's adjuvant (Days 17 and 31) or intramuscularly without adjuvant (Days 57 and 85). To detect anti-$GD_3$ rabbit antibodies by ELISA, 96-well plates were coated with purified melanoma $GD_3$ and blocked with 5% non-fat milk. Dilutions of rabbit serum were added for 1 hour. After washing, alkaline phosphatase-conjugated anti-rabbit IgG was added. Binding was visualized by adding substrate (p-nitrophenyl-phosphate) and measuring the absorbance at 410 nm.

Figure 7:
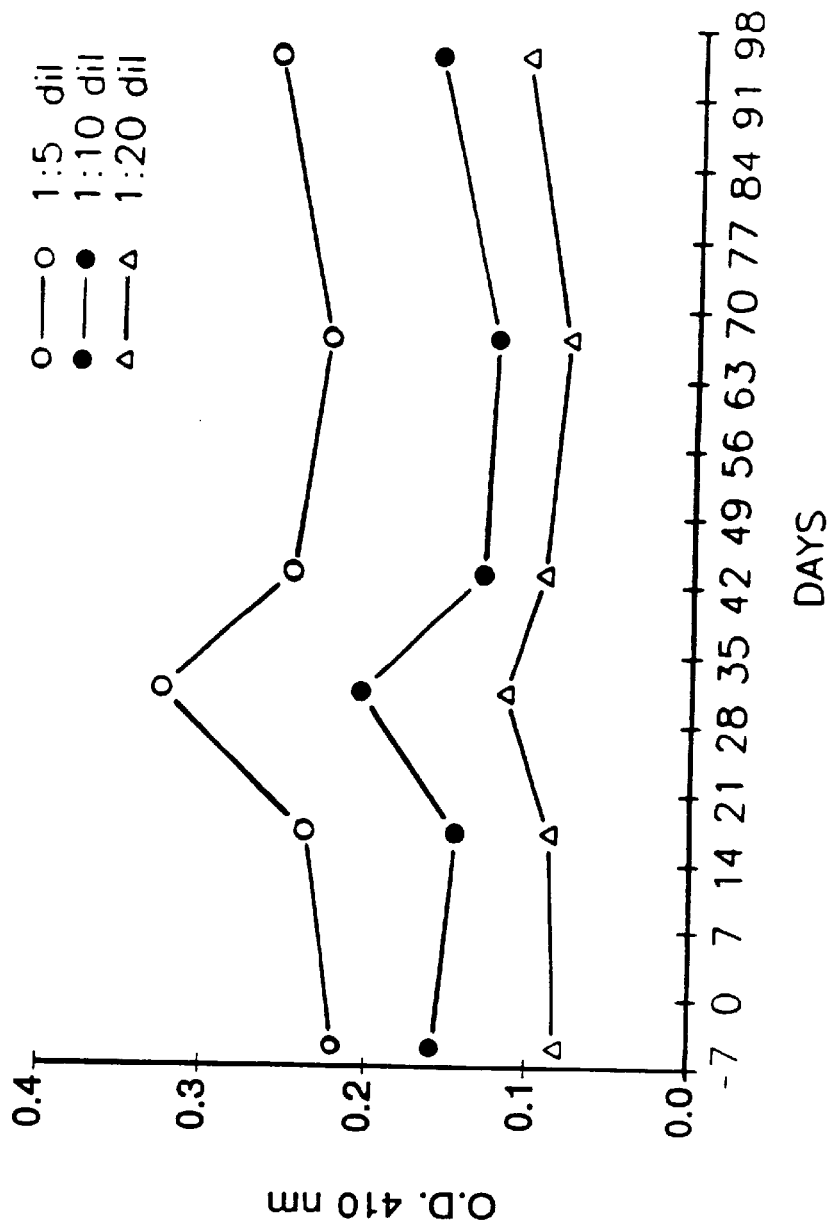

FIG. 7: Anti-GD$_3$ IgM of Rabbit 545 by ELISA. Rabbit 545 developed IgM after being immunized with BEC2 mixed with Freund's complete adjuvant. The response was measured by ELISA.

Figure 8:
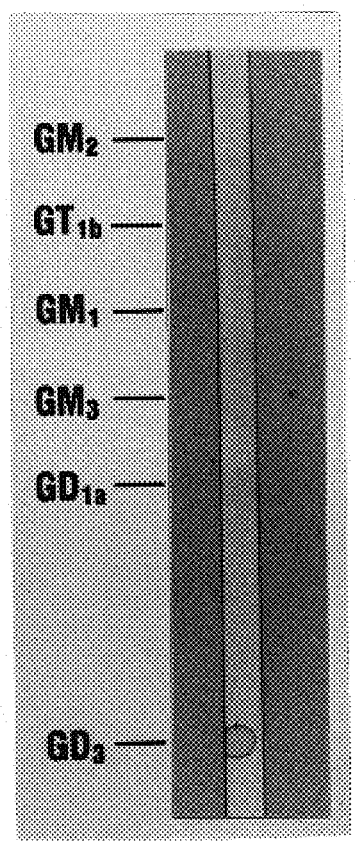

FIG. 8: Anti-GD$_3$ antibodies induced by BEC2 do not cross-react with other gangliosides. 1 μg of various purified gangliosides were applied to strips of nitrocellulose filters and allowed to dry. The strips were blocked in 5% non-fat milk and washed. Strips were incubated in rabbit serum (diluted 1:10) overnight. After washing, peroxidase-conjugated anti-rabbit IgM was added for 2 hours. The strips were again washed and binding was visualized by adding 4-chloro-1-naphthol substrate with $H_2O_2$.

Figure 9:
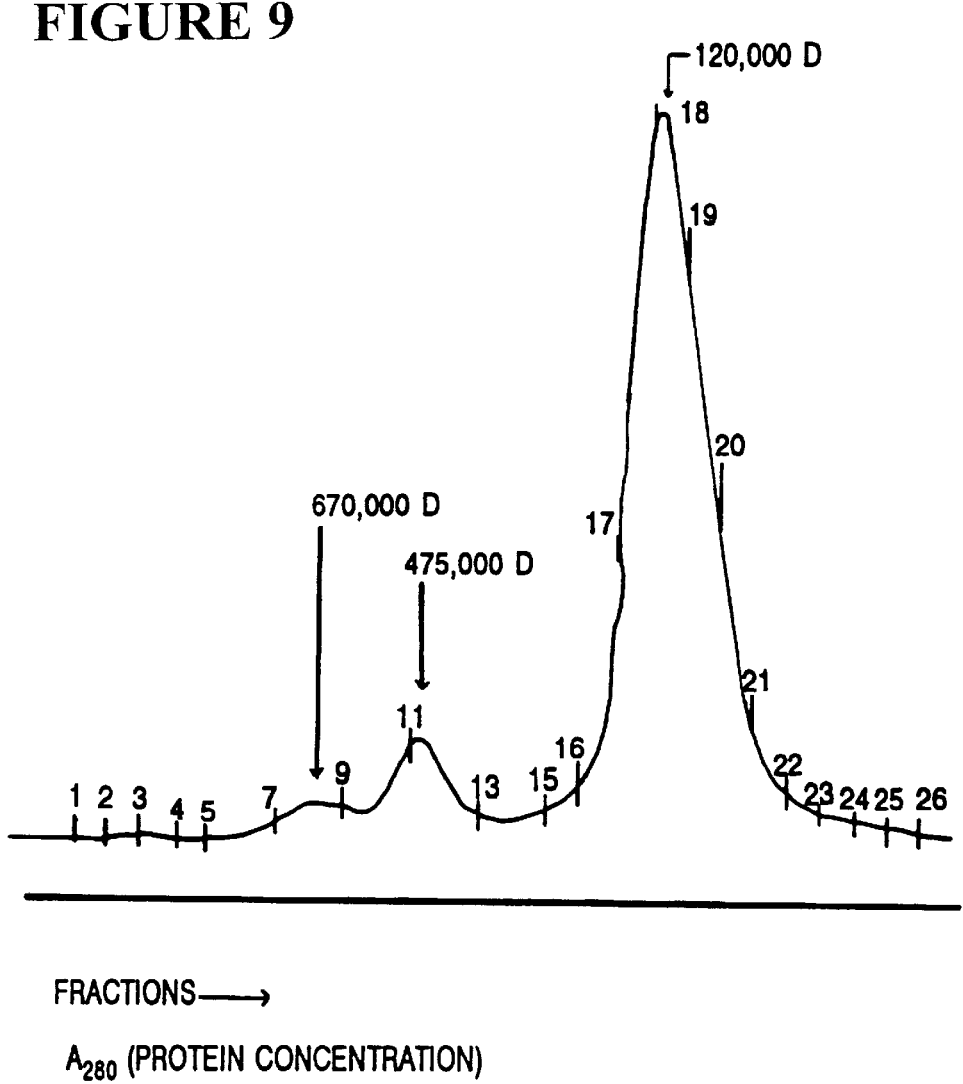

FIG. 9: Chromatogram showing that most proteins eluted at a molecular weight of approximately 120 kD which is consistent with IgG (145–150 kD) but not consistent with IgM (900 kD).

Figure 10:
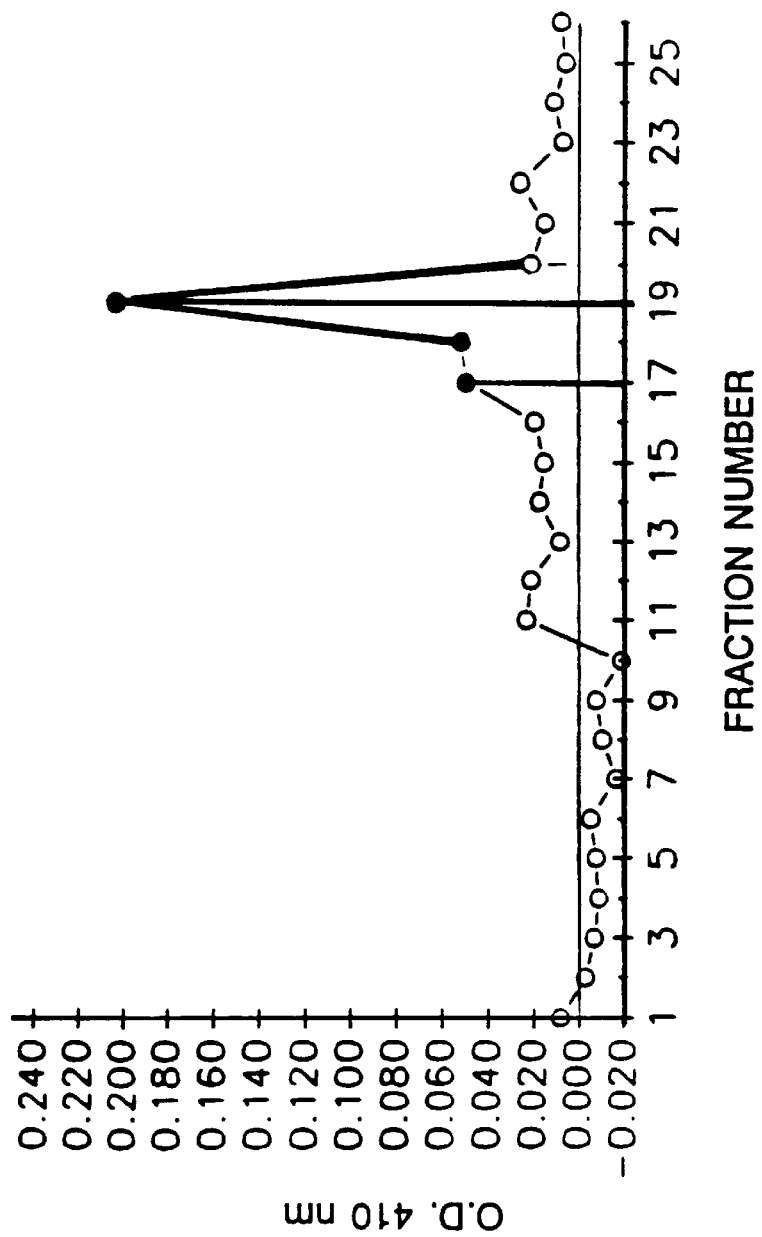

FIG. 10: Anti-GD$_3$ reactivity of $NH_4So_4$ precipitate from Rabbit 543. Graph showing the anti-GD$_3$ reactivity of each fraction. It is clear that only the 120 kD fraction is bound to GD$_3$.

FIG. 11: R24 comprises a known mixture of three variant antibody species designated V1-R24, V2-R24, and R24. The V1-R24 and V2-R24 variants comprise one and two irrelevant antibody light chains, respectively; in contrast, R24 comprises relevant light chains.

DETAILED DESCRIPTION OF THE INVENTION

The present invention provides an anti-idiotypic antibody, such as a polyclonal but preferably a monoclonal antibody, which induces an immune response against a glycosphingolipid. As used herein glycosphingolipids and gangliosides are either naturally-occurring or synthetic molecules.

In one instance the glycosphingolipid is a ganglioside, e.g. GD$_3$, GD2, GM2, and GM3. GD$_3$ is preferred.

Generally, an antibody comprises two molecules, each molecule having two different polypeptides, the shorter of which functions as the light chains of the antibody and the longer of which polypeptides function as the heavy chains of the antibody. However, as used herein, antibody is given a functional definition, i.e. any molecule, whether naturally-occurring, artificially induced, or recombinant, which has specific immunoreactive activity. Normally, as used herein, an antibody will include at least one variable region from a heavy or light chain. Additionally, the antibody may comprise combinations of variable regions. The combination may include more than one variable region of a light chain or of a heavy chain. The antibody may also include variable regions from one or more light chains in combination with variable regions of one or more heavy chains.

Accordingly, a fragment of a naturally occurring or recombinant antibody molecule is encompassed within the scope of this invention. As used herein a Fab protein of a F(ab')2 protein which exhibits immunoreactive activity is an antibody. Also, as used herein, an immunologically reactive complex comprising two different polypeptides, the shorter of which function as a light chain and the longer of which function as a heavy chain is an antibody. Further, as used herein, a variable region fragment (Fv region) is also an antibody.

Further, in one example, the immunologically reactive complex may be produced by known genetic engineering methods or otherwise (4, 8, 9, 5, 10).

In another example, the previously described anti-idiotypic antibody, preferably monoclonal antibody, which specifically induces an immune response against the GD$_3$ ganglioside also specifically binds to the binding site of the R24 antibody.

The genetically engineered anti-idiotypic antibody of this invention may be derived from any mammal. The genetically engineered anti-idiotypic antibody may also be a chimeric antibody derived from a combination of different mammals. The mammal may be, for example, a rabbit, a mouse, a rat, a goat, or a human. The combination of different mammals includes fragments from human and mouse sources.

The antibody class and sub-class is not critical. Any sub-class may be used to prepare the anti-idiotypic antibodies of the invention. The antibodies may also contain fragments from antibodies of different classes and sub-classes, thereby forming a composite. In one preferred embodiment of the invention, the above-described anti-idiotypic antibody is an IgG class anti-idiotypic antibody.

In one example, the previously-described anti-idiotypic antibody, preferably monoclonal, is designated BEC2. The present invention also provides a hybridoma which produces any of the above-described anti-idiotypic antibodies. The hybridoma that produces BEC2 is designated BEC2 hybridoma. The BEC2 hybridoma has been deposited pursuant to the Budapest Treaty On the International Recognition Of The Deposit of Microorganisms For The Purposes of Patent Procedure with the Patent Culture Depository of the American Type Culture Collection (ATCC), 12301 Parklawn Drive, Rockville, Md. 20852 U.S.A. under ATCC Accession No. HB 10153. The present invention further provides an anti-idiotypic antibody produced by the BEC2 hybridoma.

In one embodiment of this invention, the anti-idiotypic antibody is labeled with a detectable marker. The detectable marker may be created by an enzyme reaction, for example, alkaline-phosphatase or horseradish peroxidase.

It would be clear to those skilled in the art that one method of attaching the subject anti-idiotypic antibody to an enzyme, would be by a modification of the periodate method (6). Alternatively, it would be clear to those skilled in the art to attach a ligand to the subject anti-idiotypic antibodies and a receptor of the ligand to the enzyme. A suitable ligand receptor combination is biotin-avidin in accordance with the method of Bayer et al. (7).

Moreover, this invention provides a method of generating the above-described anti-idiotypic antibody, for example BEC2, which comprises: (a) preparing an antibody, preferably a monoclonal antibody, against a glycosphingolipid, more specifically against a ganglioside, and more specifically against GD$_3$; (b) purifying the antibody; (c) attaching the antibody, such as R24, to a carrier so as to produce an immunogen; (d) combining the immunogen with a cytokine so as to produce a novel immunogen-cytokine combination; and (e) injecting the novel immunogen-cytokine combination into a mammal thereby producing the anti-idiotypic antibody.

In accordance with the practice of the invention the carrier may be any material which when combined with the antibody is immunogenic. The carrier may be a microbe, a liposome, or a proteosome. In one example the microbe is *S. aureus*.

Additionally, in accordance with the practice of the invention the cytokine may be an interleukin, preferably interleukin 1. In one example, interleukin 1 is recombinant human interleukin 1.

GD$_3$ is poorly immunogenic in man. In contrast, the subject anti-idiotypic antibodies are strongly immunogenic.

The present invention provides vaccine comprising any of the anti-idiotypic antibodies, in particular BEC2, and a pharmaceutically acceptable carrier. These vaccines are highly potent and commercially useful therapeutics.

Examples of suitable carriers are well known in the art and may include, but are in no way and are not intended to be limited to, any of the standard pharmaceutical carriers such as a phosphate buffered saline solutions, water, emulsions such as oil/water emulsion, and various types of wetting agents. Other carriers may also include sterile solutions, tablets, coated tablets, and capsules.

Typically such carriers contain excipients such as starch, milk, sugar, certain types of clay, gelatin, stearic acid or salts thereof, magnesium of calcium sterate, talc, vegetable fats or oils, gums, glycols, or other known excipients. Such carriers may also include flavor and color additives or other ingredients. Compositions comprising such carriers are formulated by well known conventional methods.

Such carriers are well known in the art and may include, but are in no way and are not intended to be limited to, any of the standard pharmaceutical carriers such as a phosphate buffered saline solutions, water, emulsions such as oil/water emulsion, and various types of wetting agents. Other carriers may also include sterile solutions, tablets, coated tablets, and capsules.

Typically such carriers contain excipients such as starch, milk, sugar, certain types of clay, gelatin, stearic acid or salts thereof, magnesium or calcium sterate, talc, vegetable fats or oils, gums, glycols, or other known excipients. Such carriers may also include flavor and color additives or other ingredients. Compositions comprising such carriers are formulated by well known conventional methods.

This invention further provides a method of immunizing a human subject against GD$_3$ gangliosides. The method comprises administering to the subject a suitable dose of the above-described vaccine. Administration of any of the vaccines may be effected by various ways. Suitable means of administration includes intravenous, intraperitoneal, subcutaneous, or intramuscular, topical, or intradermal administration.

Additionally, this invention provides a method of treating a human subject with a neoplastic or preneoplastic condition associated with the expression of glycosphingolipids, for example gangliosides such as GD3. The method comprises administering to the subject an effective amount of any of the previously-described anti-idiotypic antibodies and a pharmaceutically acceptable carrier. Examples of neoplastic and preneoplastic conditions associated with expression of GD$_3$ gangliosides include a condition selected from a group consisting of a melanoma, squamous cell carcinoma, glioblastoma, sarcoma, T cell leukemia and lymphoma, Hodgkin's disease, small cell carcinoma of the lung, or brain tumor.

In one example, administration of the previously-described anti-idiotypic antibody is effected by intravenous administration. In another example of the invention, administration of the previously-described anti-idiotypic antibody is effected by intraperitoneal administration. In yet another example, administration of the previously-described anti-idiotypic antibody is effected by subcutaneous administration. In still another example of the invention, administration of the previously-described anti-idiotypic antibody is effected by intramuscular administration. Further, in another example of the invention, administration of the previously-described anti-idiotypic antibody is effected by topical administration. Additionally, in yet another example, administration of the previously-described anti-idiotypic antibody is effected by intradermal administration.

This invention also provides a method of inhibiting a microbial infection, such as an endotoxin-related infection, in a subject which comprises priming the subject with an effective amount of the previously-described vaccine in order to generate an antibody which specifically binds to a glycosphingolipid on a microbial membrane, the antibody and the glycosphingolipid forming a combination and thereby inhibiting the microbial infection.

Additionally, this invention provides a method for inhibiting a malignancy associated with expression of GD$_3$ gangliosides in a subject such as a human subject. The method comprises priming the subject with an effective amount of the previously-described vaccine in order to generate an antibody which specifically binds to a GD$_3$ ganglioside, the antibody and the GD$_3$ ganglioside forming a combination and thereby inhibiting a malignancy associated with expression of GD$_3$ gangliosides. Examples of malignancies associated with expression of GD$_3$ gangliosides include a malignancy selected from a group consisting of a melanoma, squamous cell carcinoma, glioblastoma, sarcoma, T cell leukemia and lymphoma, Hodgkin's disease, small cell carcinoma of the lung, or brain tumor.

In one example, the method for measuring expression levels of GD$_3$ gangliosides in tissue from a subject is effected by determining the amount and distribution of GD$_3$ in tissue sections from a neoplastic tissue to be tested. The method comprises contacting the tissue to be tested with the R24 antibody and thereby detecting the expression level and distribution of GD$_3$.

The present invention provides a method of treating a subject suffering from a malignancy associated with expression of GD$_3$ gangliosides on malignant cells. The method comprises administering to the subject a cell killing amount of an anti-GD3 antibody labeled with a cytotoxic agent, such as a radioisotope, a drug, or a heavy metal. The labeled antibody binds to GD3 ganglioside, after which the cytotoxic agent kills the malignant cells to which the GD3 ganglioside is attached. It is important to eliminate unbound antibody labeled with a cytotoxic agent quickly. Elimination may be expedited by contacting the unbound labeled antibody with any of the previously-described anti-idiotypic antibodies. The anti-idiotypic antibodies bind the previously unbound labeled antibody so as to form a complex which may be cleared by excretion from the subject. In this way the subject is treated for the malignancy without undue harm by the cytotoxic agent.

It would be well known to those skilled in the art that "clearing" undesirable composites, in particular the labeled complex, would involve transport of the complex to the spleen, lung, or liver, wherein an Fc region of the antibody within the composite would bind to the Fc receptor of spleen, lung, or liver tissues or cells derived therefrom. After binding to these tissues or the cells derived therefrom, the complex is excreted from the body by physiological or biochemical means.

Examples of a malignancy associated with the expression of GD$_3$ gangliosides includes any malignancy selected from a group consisting of a melanoma, squamous cell carcinoma, glioblastoma, sarcoma, T cell leukemia and lymphoma, Hodgkin's disease, small cell carcinoma of the lung, or brain tumor.

This invention additionally provides a method of inhibiting the proliferation of cells associated with elevated levels of $GD_3$ gangliosides in a subject. The method comprises administering to the subject an effective amount of the previously-described vaccine.

Further, this invention provides an immunogenic composition of matter comprising an effective amount of a cytokine, e.g. interleukin 1, preferably recombinant human interleukin 1, and a melanoma ganglioside-specific antibody, such as a R24 antibody, attached to a carrier. Further, the carrier may be a microbe, preferably *S. aureus*.

Additionally, the present invention provides a method of generating an anti-idiotypic antibody which comprises: (a) attaching an antigen, for example R24, to a microbe thereby obtaining an immunogen; (b) purifying the immunogen; (c) combining the immunogen with interleukin 1 so as to produce an immunogen-interleukin 1 combination; and (d) injecting the immunogen-interleukin 1 combination into mice, preferably syngeneic mice, thereby generating the anti-idiotypic antibody.

Finally, this invention is illustrated in the Experimental Details section which follows. This section is set forth to aid in an understanding of the invention but is not intended to, and should not be construed to, limit in any way the invention as set forth in the claims which follow.

Experimental Details

Anti-idiotypic mAbs to R24

We immunized syngeneic (C57B1/6X BALB/C)F1 female mice with purified R24 free of variants V1-R24 and V2-R24. The significance of using syngeneic mice is that the only portion of the R24 molecule which should be recognized as foreign is the paratope. It is standard to mix the immunizing material with an "adjuvant", a potentiator of an immune response, which boosts the immune response of the mouse. The novel adjuvant disclosed herein was made by sticking the R24 onto *S. aureus* cells and injecting the R24-coated cells along with rh IL-1 (DuPont).

The mice received two weekly boosts. Three days before fusion, mice were injected with 50 μg R24 i.v. Splenocytes were fused with SP2/0 using standard techniques. Hybridomas were screened for the ability to bind to R24 $F(ab')_2$ fragments using an alkaline phosphatase conjugated goat anti-mouse $F_c$-specific second antibody. Positive colonies were subcloned twice by limiting dilution. Both *S. aureus* and IL-1 are strong stimulators of B lymphocytes. Using standard hybridoma techniques and fusion of immune mouse spleen cells to the SP2/0 mouse myeloma cell line BEC2 and BEC3 were produced.

Demonstrating that BEC2 is an Anti-idiotypic mAb

BEC2 recognizes unique determinants on R24

If BEC2 is indeed an anti-idiotype for R24, it would be expected that BEC2 would bind only to R24 and no other mAb. We have tested the ability of BEC2 to bind to 23 other mAbs using an inhibition assay. No mAb, other than R24, can compete with R24 for BEC2 binding (Table 1). It is notable that V1-R24, the variant with two irrelevant light chains, is not bound by BEC2. This is consistent with the model that BEC2 recognizes the paratope of R24.

Figure 1:
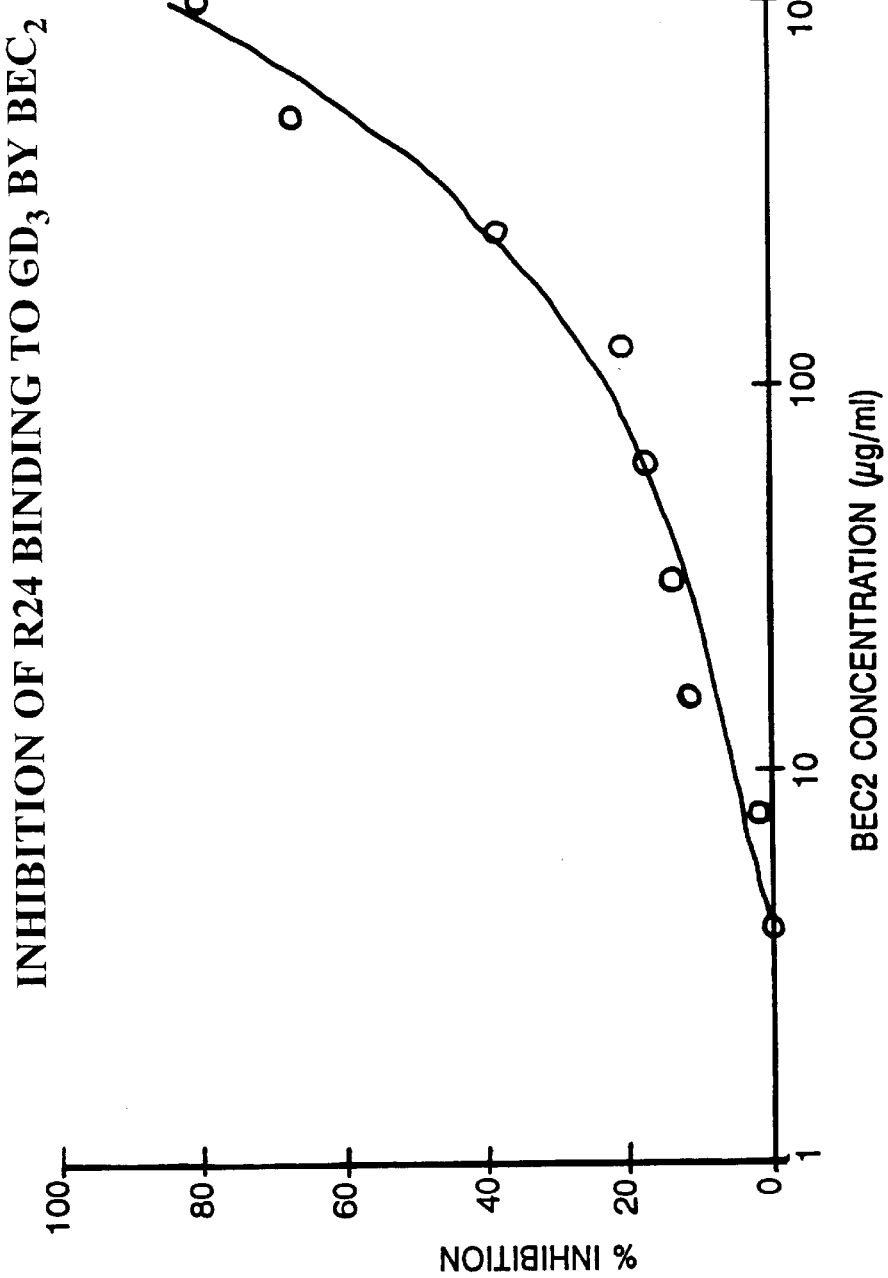
FIG. 1: Inhibition of R24 binding to $GD_3$ by BEC2. Dilutions of BEC2 were incubated with 5 µg/ml of biotinylated R24 for 1 hour. The mixture was then plated into wells coated with melanoma gangliosides containing $GD_3$. Binding of R24 was detected by adding alkaline phosphatase-conjugated avidin for 15 minutes. After washing, substrate (p-nitrophenylphosphate) was added and the absorbance at 410 nm was measured.
Figure 3:
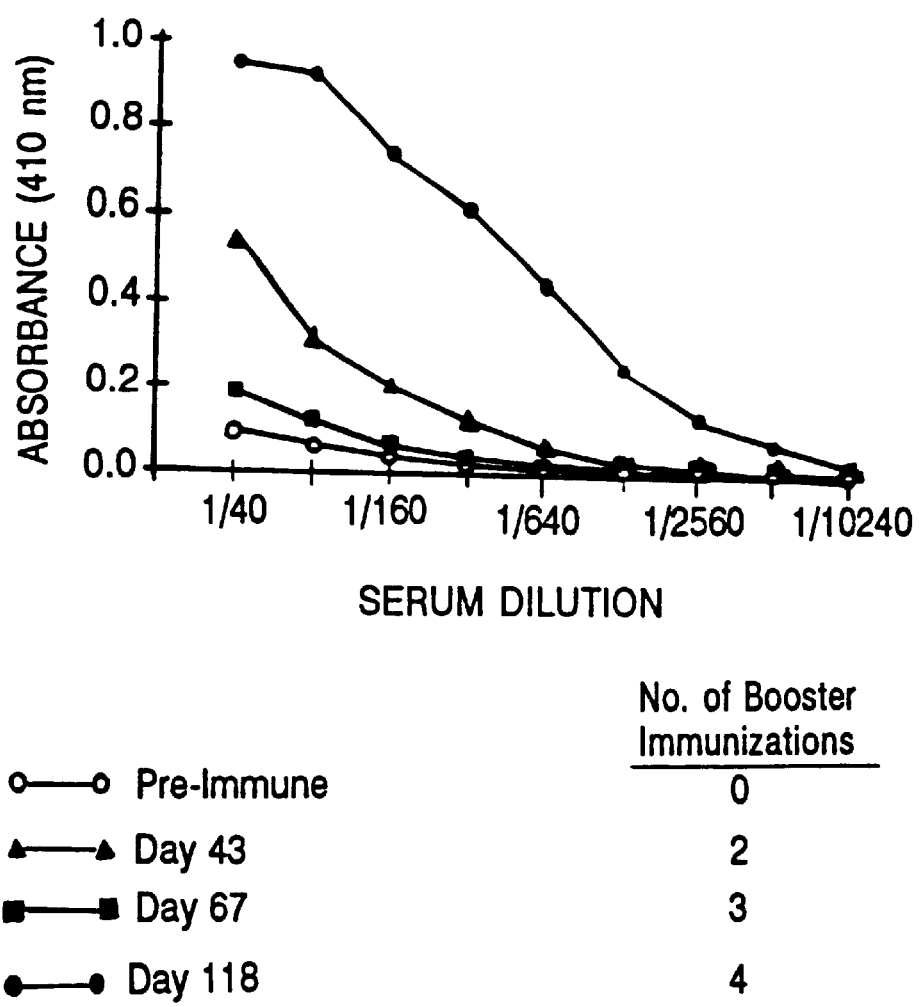
FIG. 3: Anti-$GD_3$ reactivity induced in rabbits by immunization with BEC2. Rabbits were inoculated subcutaneously with 100 µl of BEC2 in complete Freund's adjuvant. Subsequent booster immunizations were administered either subcutaneously in incomplete Freund's adjuvant (Days 17 and 31) or intramuscularly without adjuvant (Days 57 and 85). To detect anti-$GD_3$ rabbit antibodies by ELISA, 96-well plates were coated with purified melanoma $GD_3$ and blocked with 5% non-fat milk. Dilutions of rabbit serum were added for 1 hour. After washing, alkaline phosphatase-conjugated anti-rabbit IgM was added. Binding was visualized by adding substrate (p-nitrophenyl-phosphate) and measuring the absorbance at 410 nm.
Figure 4:
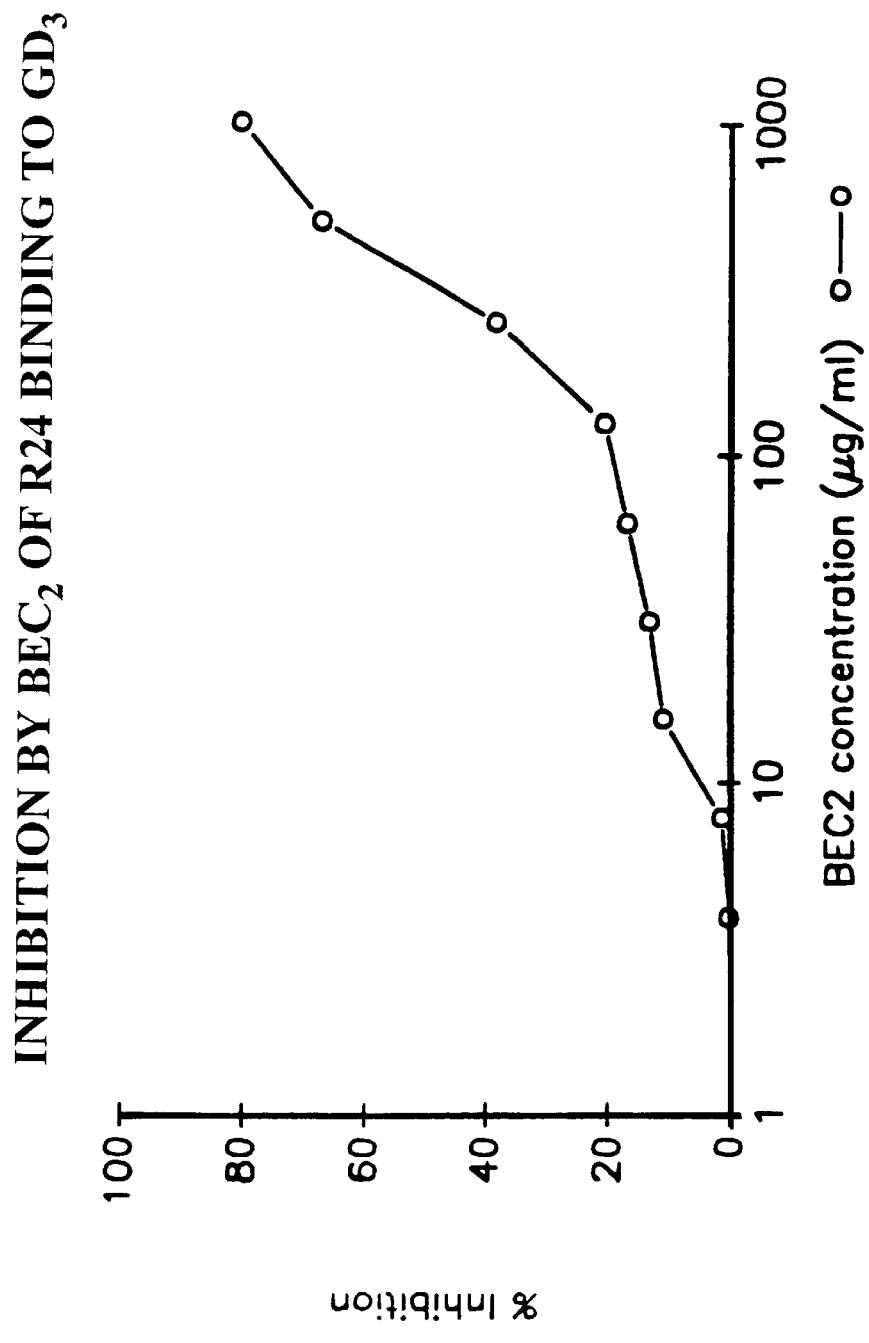
FIG. 4: Inhibition by BEC2 or R24 binding to $GD_3$. Data shows significant inhibition of R24 binding to $GD_3$ by BEC2, this is consistent with BEC2 being an Ab 2b anti-idiotypic mAb.

The results in Table 1 were obtained using the following method. BEC2 (5 μg/ml) was pre-incubated with dilutions of inhibiting mAb for 1 hr. The mixture was then, plated into wells previously coated with R24 $F(ab')_2$ fragments and blocked with 5% non-fat milk. BEC2 binding was detected by ELISA using an alkaline phosphatase-conjugated second antibody specific for the $F_c$ region. BEC2 carries the internal image of the original antigen $GD_3$ An anti-idiotypic mAb which recognizes the paratope of the immunizing mAb is called an Ab2b anti-idiotypic mAb. One implication of this is that the paratope of BEC2 should mimic $GD_3$. If one imagines the R24 paratope as a template for $GD_3$, and both $GD_3$ and BEC2 fit that template, then BEC2 must resemble $GD_3$. Using serological assays, we show that BEC2 can inhibit the binding of R24 to $GD_3$. FIG. 4 shows the results on one experiment in which different concentrations of BEC2 were preincubated with a fixed dilution of biotinylated R24. The mixture was added to a well coated with $GD_3$ and the amount of R24 available for binding was measured by adding alkaline phosphatase-conjugated avidin. The data show significant inhibition of R24 binding to $GD_3$ by BEC2 which is consistent with BEC2 being an Ab2b anti-idiotypic mAb. In order to directly demonstrate that the paratope of BEC2 mimics $GD_3$, it is necessary to immunize animals with BEC2 and show that the animals develop antibodies to $GD_3$.

We immunized four New Zealand White Rabbits with BEC2 mixed with Freund's complete adjuvant. The animals received several booster immunizations mixed with Freund's incomplete adjuvant

TABLE 1

Ability of BEC2 to bind to various monoclonal antibodies as measured by the ability of the monoclonal antibody to prevent binding of BEC2 to R24. Inhibition of BEC2 binding to R24 $F(ab')_2$ Fragments by a Panel of mAb.

| Antibody | Isotype | Specificity | IC50[1] |
|---|---|---|---|
| 1. MOPC104E | M | &1→>3 dextrans | 390 |
| 2. TEPC183 | M | ND[2] | 425 |
| 3. MOPC315 | A | Dinitrophenol . . . | >900 |
| 4. TEPC15 | A | Phosphoryl choline | >900 |
| 5. MOPC21 | G1 | ND | >700 |
| 6. HT29-15 | G1 | Adenocarcinoma | >900 |
| 7. 455 | G1 | EGF receptor | >900 |
| 8. M111 | G1 | gp110 | 465 |
| 9. S22 | G1 | ND | >1000 |
| 10. 2G10 | G1 | gp76 | >1000 |
| 11. C350 | G1 | gp180 | >500 |
| 12. UPC10 | G2a | b2-6 fructosan | >900 |
| 13. TA99 | G2a | gp75 | >900 |
| 14. A33 | G2a | ND | >900 |
| 15. M195 | G2a | CD33 | >1000 |
| 16. F23 | G2a | CD13 | >1000 |
| 17. MOPC141 | G2b | ND | 485 |
| 18. OKB7 | G2b | CD21 | >1000 |
| 19. FLOPC21 | G3 | ND | >900 |
| 20. Y5606 | G3 | AMP/purine/tri-ethanolamine | >500 |
| 21. F36/22 | G3 | Breast Carcinoma | >1000 |
| 22. 3F8 | G3 | GD2 ganglioside | >1000 |
| 23. V1-R24[3] | G3 | $GD_3$ ganglioside | 425 |
| 24. R24 | G3 | $GD_3$ ganglioside | 26 |

[1]$IC_{50}$ is the concentration of inhibiting mAb(in 1 g/ml) required to inhibit 50% of BEC2 binding to R24 $F(ab')_2$ fragments.
[2]Not Determined
[3]A variant of R24 in which both light chains are replaced with MOPC 21 myeloma light chains. This results in a mAb with >40-fold lower affinity for $GD_3$.

over approximately three months. The rabbits were bled periodically and the serum was assayed for ant-$GD_3$ reactivity using two different assays. The anti-$GD_3$ IgG response was measured by radioimmunoassay (RIA) using [$^{125}$I]-Protein A. The anti-$GD_3$ IgM response was measured by ELISA using alkaline phosphatase-conjugated goat anti-rabbit second antibody which was specific for the mu chain. The specificity of both the IgG and IgM response was analyzed by immunoblot assays against several gangliosides. In these assays, [$^{125}$I]-Protein A was used to visualize IgG binding while peroxidase-conjugated goat anti-rabbit (mu chain specific) antiserum was used to visualize IgM binding.

Figure 5:
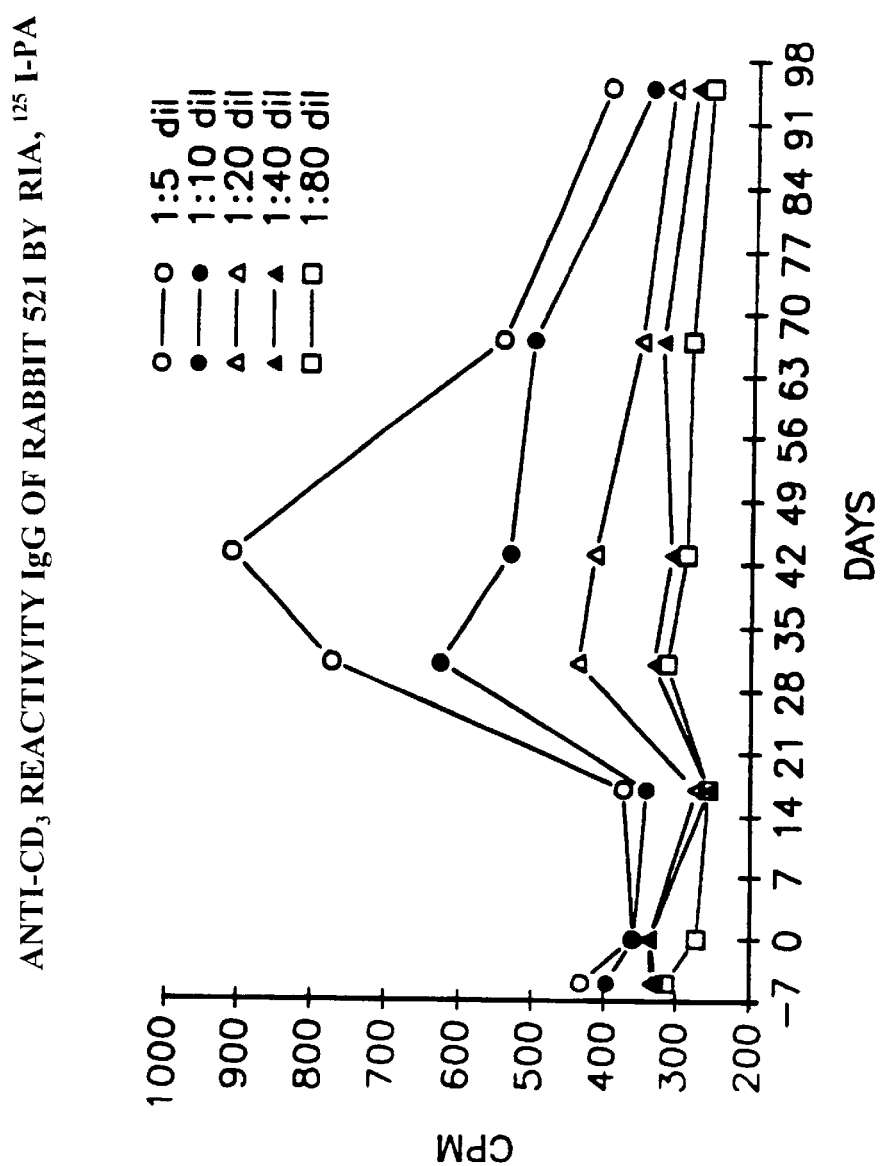
FIG. 5: Anti-$GD_3$ IgG of Rabbit 521 by RIA. Rabbit 521 developed IgG against $GD_3$ after being immunized with BEC2 mixed with Freund's complete adjuvant. The response was measured by RIA.
Figure 6:
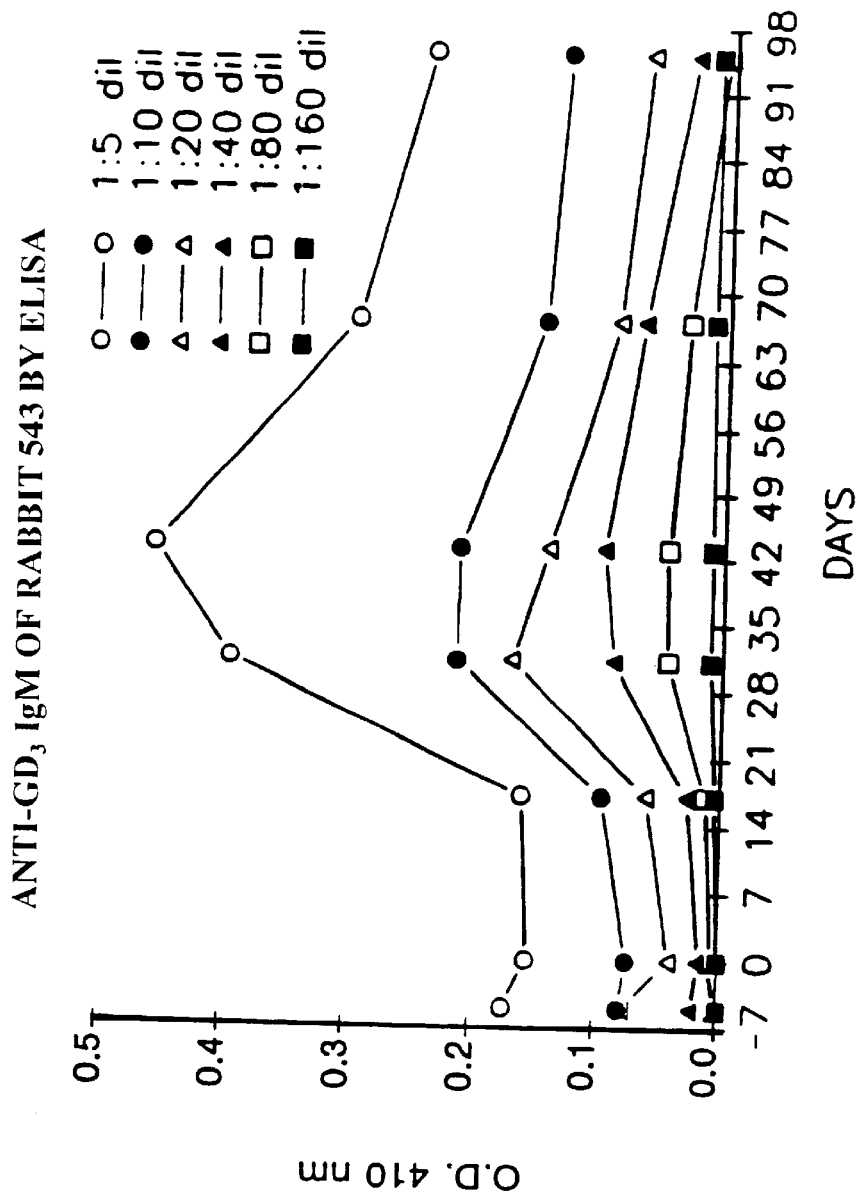
FIG. 6: Anti-$GD_3$ IgM of Rabbit 543 by ELISA. Rabbit 543 developed IgM after being immunized with BEC2 mixed with Freund's complete adjuvant. The response was measured by ELISA.

At least three of the four rabbits developed an anti-$GD_3$ antibody response. By RIA, Rabbit 521 developed IgG against $GD_3$ (FIG. 5) although by immunoblotting, all four rabbits appeared to make anti-$GD_3$ IgG. By ELISA, rabbits 543 (FIG. 6) and 545 (FIG. 7) developed IgM. The specificity of this antibody response was analyzed by immunoblot. FIG. 8 shows that IgM from rabbit 543 binds to $GD_3$ but not to the other five gangliosides tested (GM1, GM2, GM3, GD1a, GT1b). As noted above, immunoblotting of serum from all four rabbits showed evidence of IgG binding to $GD_3$ and this binding was specific.

In order to confirm that this anti-$GD_3$ reactivity was indeed IgG, serum from rabbit 543 was precipitated using 45% $NH_4SO_4$ and the immunoglobulin salted out was fractionated by size exclusion chromatography (Superose 6 column, Pharmacia). FIG. 9 shows that most of the protein eluted at a molecular weight of approximately 120 kD which is consistent with IgG (145–150 kD) but not consistent with IgM (900 kD). FIG. 10 shows the anti-$GD_3$ reactivity of each fraction and it is clear that only the 120 kD fraction bind to $GD_3$.

Results

BEC2 binds to the Fab region of R24 and blocks R24 binding to $GD_3$ gangliosides. Additionally, BEC2 binds to two anti-$GD_3$ monoclonal antibodies. C5(IgG3) and K9 (IgM). Because BEC2 contains irrelevant light chains BEC2 neither binds to other mouse monoclonal antibodies, including four IgG3 monoclonal antibodies, nor binds to the variant of R24.

BEC2 is an AB2 anti-idiotypic monoclonal antibody for it binds to the portion of R24 which recognizes $GD_3$. If one imagines the R24 binding site as a template for $GD_3$, and both $GD_3$ and BEC2 fit that template, then BEC2 must resemble $GD_3$. Using serological assays, we have shown that BEC2 does indeed resemble $GD_3$. BEC2 is a useful way to immunize against $GD_3$, and thus, important as a vaccine against melanoma and other tumors.

To demonstrate that BEC2 carries an internal image of $GD_3$, we immunized NZW rabbits with BEC2 and studied pre-immune and immune sera for evidence of anti-$GD_3$ reactivity. Immunized rabbits developed an antibody response to $GD_3$ detectable by ELISA and Immunoblot against purified $GD_3$, and by mixed hemadsorption assay against a $GD_3$+ human melanoma cell line. Specificity analysis showed that immune sera recognized only $GD_3$ and not $GM_1$, $GM_2$, $GM_3$, $GD_{1a}$, or $GT_{1b}$, monoclonal antibody BEC2 provides a strategy for active immunization of melanoma patients against $GD_3$.

Immunization with BEC2 induces high titer, specific IgM and IgG antibodies to $GD_3$ in rabbits and IgM antibodies in syngeneic (BALB/c×C57B1)F1 mice.

From the experiments, we find that BEC2 is a mouse IgG2b anti-idiotypic mAb directed against R24 and binds the antigen-binding site of R24. Further, immunization of rabbits with BEC2 results in an IgM and IgG response against $GD_3$. Finally, BEC2 carries the internal image of the ganglioside $GD_3$, therefore, it is useful for immunization against $GD_3$ gangliosides.

REFERENCES

1. T. Tai et al. (1995) *Int. S. Cancer*, 35:607.
2. G. Viale et al. (1987) *Journal of Immunology*, 139:4250.
3. K. E. Stein and T. Soderstrom (1984) *Journal of Experimental Medicine*, 160:1001.
4. Morrison, S. L. et al. (1988) *Clin. Chem.* 34:1668.
5. Morrison, S. L. et al. (1987) *Ann. N.Y. Acad. Sci.* 507:187.
6. Oi, V. T., and Morrison, S. L. (1986) *BioTechniques* 4:214.
7. Wilson, M. B. and Nakane, P. K. (1978) *Immunofluorescence and Related Staining Techniques* (Elsevier/North Holland Biomedical Press, Amsterdam) 215.
8. Bayer et al. (1979) *Methods in Enzymology*, 62:308.
9. Neuberger, et al. (1984) *Nature* (London), 312:604;
10. Neuberger, M. J. et al. (1985) *Nature* (London), 314:268–270.

What is claimed is:

1. A method for generating in a subject an immune response against ganglioside $GD_3$ by administering to the subject anti-idiotypic antibody BEC-2 (ATCC No. HB 10153).

* * * * *

UNITED STATES PATENT AND TRADEMARK OFFICE
CERTIFICATE OF CORRECTION

PATENT NO. : 6,805,862 B1
DATED : October 19, 2004
INVENTOR(S) : Paul B. Chapman and Alan N. Houghton It is certified that error appears in the above-identified patent and that said Letters Patent is hereby corrected as shown below:

<u>Title page,</u>
Item [73], Assignee, "Sloan-Kattering" should read -- Sloan-Kettering --.

Signed and Sealed this

Eleventh Day of January, 2005

JON W. DUDAS
*Director of the United States Patent and Trademark Office*